(12) United States Patent
Haibach et al.

(10) Patent No.: US 10,874,815 B2
(45) Date of Patent: Dec. 29, 2020

(54) PATIENT INTERFACE DEVICE AND RETENTION ASSEMBLY THEREFOR

(71) Applicant: KONINKLIJKE PHILIPS N.V., Eindhoven (NL)

(72) Inventors: Richard Thomas Haibach, Verona, PA (US); Stephen George Hlopick, Murrysville, PA (US); Robert Edward O'Grady, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 346 days.

(21) Appl. No.: 15/580,860

(22) PCT Filed: Jun. 15, 2016

(86) PCT No.: PCT/IB2016/053511
§ 371 (c)(1),
(2) Date: Dec. 8, 2017

(87) PCT Pub. No.: WO2016/203376
PCT Pub. Date: Dec. 22, 2016

(65) Prior Publication Data
US 2018/0140796 A1    May 24, 2018

Related U.S. Application Data

(60) Provisional application No. 62/181,353, filed on Jun. 18, 2015.

(51) Int. Cl.
*A61M 16/06*    (2006.01)
*A61M 11/00*    (2006.01)

(52) U.S. Cl.
CPC ........ *A61M 16/0683* (2013.01); *A61M 11/00* (2013.01); *A61M 16/0622* (2014.02)

(58) Field of Classification Search
CPC .............. A61M 11/00; A61M 16/0622; A61M 16/0683; A61M 16/0816; A61B 18/084;
(Continued)

(56) References Cited

U.S. PATENT DOCUMENTS 6,292,985 B1 * 9/2001 Grunberger ........ A44B 11/2592
24/303
6,550,070 B2 * 4/2003 Wiegand .............. A62B 18/084
128/207.11
(Continued)

FOREIGN PATENT DOCUMENTS

WO    WO2012028994 A1    3/2012
WO    WO2014053987 A1    4/2014
WO    WO-2015079396 A1 *  6/2015    ........ A61M 16/0816

*Primary Examiner* — Samchuan C Yao
*Assistant Examiner* — Nathan M Le
(74) *Attorney, Agent, or Firm* — Michael W. Haas

(57) ABSTRACT

A retention assembly is for a patient interface device. The patient interface device includes a cushion member structured to engage a face of a patient. The retention assembly includes: a retention member structured to be coupled to the cushion member; a headgear member; a first interconnect member removably coupled to the retention member; and a second interconnect member removably coupled to the headgear member. The second interconnect member is removably coupled to the first interconnect member in order to couple the headgear member to the retention member.

11 Claims, 8 Drawing Sheets

(58) Field of Classification Search
CPC ........... A42B 1/24; A42B 1/242; A42B 1/244; A42B 1/245; A42B 1/247; A42B 3/30
See application file for complete search history.

(56) References Cited

U.S. PATENT DOCUMENTS

| | | | | |
|---|---|---|---|---|
| 6,598,271 B2* | 7/2003 | Nire | ......................... | A41F 1/002 24/265 WS |
| 6,598,272 B2* | 7/2003 | Nire | ......................... | A41F 1/002 24/265 WS |
| 6,606,767 B2* | 8/2003 | Wong | ...................... | A41F 1/006 24/303 |
| 6,647,597 B2* | 11/2003 | Reiter | ..................... | A41F 1/002 24/303 |
| 7,406,965 B2* | 8/2008 | Kwok | ................... | A61M 16/06 128/201.23 |
| 8,770,197 B2* | 7/2014 | Guney | ................... | A61M 16/06 128/206.21 |
| 2001/0010778 A1* | 8/2001 | Hilton | ..................... | F16B 21/08 403/321 |
| 2004/0045551 A1* | 3/2004 | Eaton | .................... | A61M 16/06 128/206.21 |
| 2004/0107547 A1* | 6/2004 | Chung | .................. | A44B 11/258 24/303 |
| 2004/0226150 A1* | 11/2004 | Beletsky | .............. | A44B 11/263 24/625 |
| 2005/0155604 A1* | 7/2005 | Ging | .................... | A44B 11/266 128/206.21 |
| 2006/0032504 A1* | 2/2006 | Burton | .................. | A61M 16/06 128/207.11 |
| 2006/0174892 A1 | 8/2006 | Leksutin | | |
| 2006/0225740 A1* | 10/2006 | Eaton | .................... | A61M 16/06 128/206.24 |
| 2007/0028919 A1* | 2/2007 | Ho | .................... | A61M 16/0683 128/204.18 |
| 2007/0157353 A1 | 7/2007 | Guney | | |
| 2008/0099023 A1* | 5/2008 | Berthon-Jones | ........................... | A61M 16/0833 128/206.24 |
| 2009/0320850 A1* | 12/2009 | Wallnewitz | ....... | A61M 16/0683 128/207.11 |
| 2010/0163049 A1* | 7/2010 | Osier | .................... | A61M 16/06 128/206.24 |
| 2010/0236559 A1 | 9/2010 | Lithgow | | |
| 2010/0258136 A1* | 10/2010 | Doherty | ............ | A61M 16/0683 128/207.17 |
| 2010/0319700 A1* | 12/2010 | Ng | ........................ | A61M 16/06 128/206.28 |
| 2011/0265796 A1* | 11/2011 | Amarasinghe | ........ | A61M 16/06 128/206.28 |
| 2012/0024291 A1 | 2/2012 | Amarasinghe | | |
| 2012/0111333 A1* | 5/2012 | Eifler | ................. | A61M 16/0683 128/205.25 |
| 2012/0285462 A1 | 11/2012 | Pierro | | |
| 2013/0233316 A1* | 9/2013 | Ng | ........................ | A61M 16/06 128/205.25 |
| 2015/0075534 A1* | 3/2015 | Gulliver | ............ | A61M 16/0688 128/207.13 |
| 2015/0114398 A1* | 4/2015 | Chodkowski | ...... | A61M 16/0816 128/206.24 |
| 2015/0202397 A1* | 7/2015 | Pastoor | ............. | A61M 16/0622 128/205.25 |
| 2015/0289598 A1* | 10/2015 | Hsiung | ................. | A62B 18/02 128/202.27 |

* cited by examiner

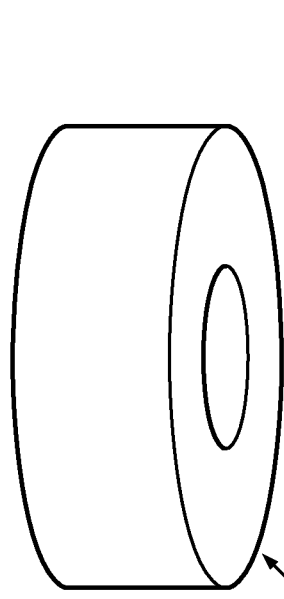
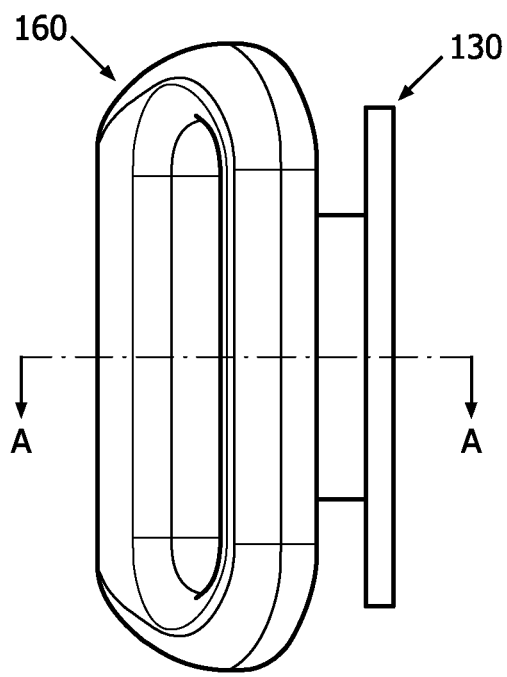
FIG. 8  FIG. 9
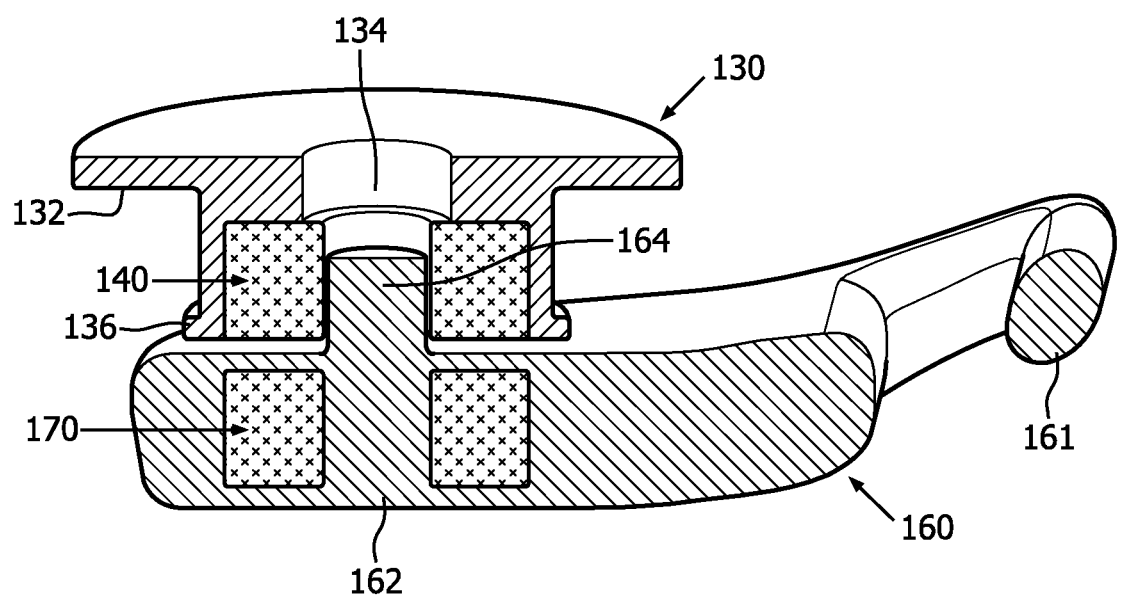
FIG. 10

PATIENT INTERFACE DEVICE AND RETENTION ASSEMBLY THEREFOR

CROSS-REFERENCE TO RELATED APPLICATIONS

This patent application claims the priority benefit under 35 U.S.C. § 371 of international patent application no. PCT/IB2016/053511, filed Jun. 15, 2016, which claims the priority benefit under 35 U.S.C. § 119(e) of U.S. Provisional Application No. 62/181,353, filed on Jun. 18, 2015, the contents of which are herein incorporated by reference.

BACKGROUND OF THE INVENTION

1. Field of the Invention

The present invention relates to patient interface devices used to deliver a flow of breathing gas to a patient. The present invention also relates to retention assemblies for patient interface devices.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible cushion on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. Such patient interface devices may also employ other patient contacting components, such as forehead supports, cheek pads and chin pads. The patient interface device is connected to a gas delivery hose and interfaces the ventilator or pressure support device with the airway of the patient, so that a flow of breathing gas can be delivered from the pressure/flow generating device to the airway of the patient.

It is known to maintain such devices on the face of a wearer by a headgear having one or more straps adapted to fit over/around the patient's head. In order to connect the headgear to the mask frame, known patient interface devices employ clips. However, during misuse conditions, such as when a clip becomes disconnected from the mask frame and/or the headgear, known clips are difficult to reconnect to the mask frame and the headgear. In operation, such as when therapy is delivered during the night, this creates an undesirable burden and an unnecessary expenditure of time, as the user will have to properly reconnect the components in the dark.

SUMMARY OF THE INVENTION

Accordingly, it is an object of the present invention to provide a retention assembly that overcomes the shortcomings of conventional clips to connect the mask frame to the headgear. This object is achieved according to one embodiment of the present invention by providing a retention assembly for a patient interface device. The patient interface device includes a cushion member structured to engage a face of a patient. The retention assembly comprises: a retention member structured to be coupled to the cushion member; a headgear member; a first interconnect member removably coupled to the retention member; and a second interconnect member removably coupled to the headgear member. The second interconnect member is removably coupled to the first interconnect member in order to couple the headgear member to the retention member.

It is yet another object of the present invention to provide a patient interface device that does not suffer from the disadvantages associated with conventional clips for attaching mask frames to headgear. This object is achieved by providing a patient interface device that includes a cushion member structured to engage a face of a patient; and a retention assembly comprising: a retention member coupled to the cushion member, a headgear member, a first interconnect member removably coupled to the retention member, and a second interconnect member removably coupled to the headgear member. The second interconnect member is removably coupled to the first interconnect member in order to couple the headgear member to the retention member.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 8 is an isometric view of a magnet for the interconnect members of FIG. 5;

FIG. 9 is a side view of the interconnect members of FIG. 5;

FIG. 10 is a section view of the interconnect members, taken along line A-A of FIG. 9;

DETAILED DESCRIPTION OF EXEMPLARY EMBODIMENTS

Figure 1:
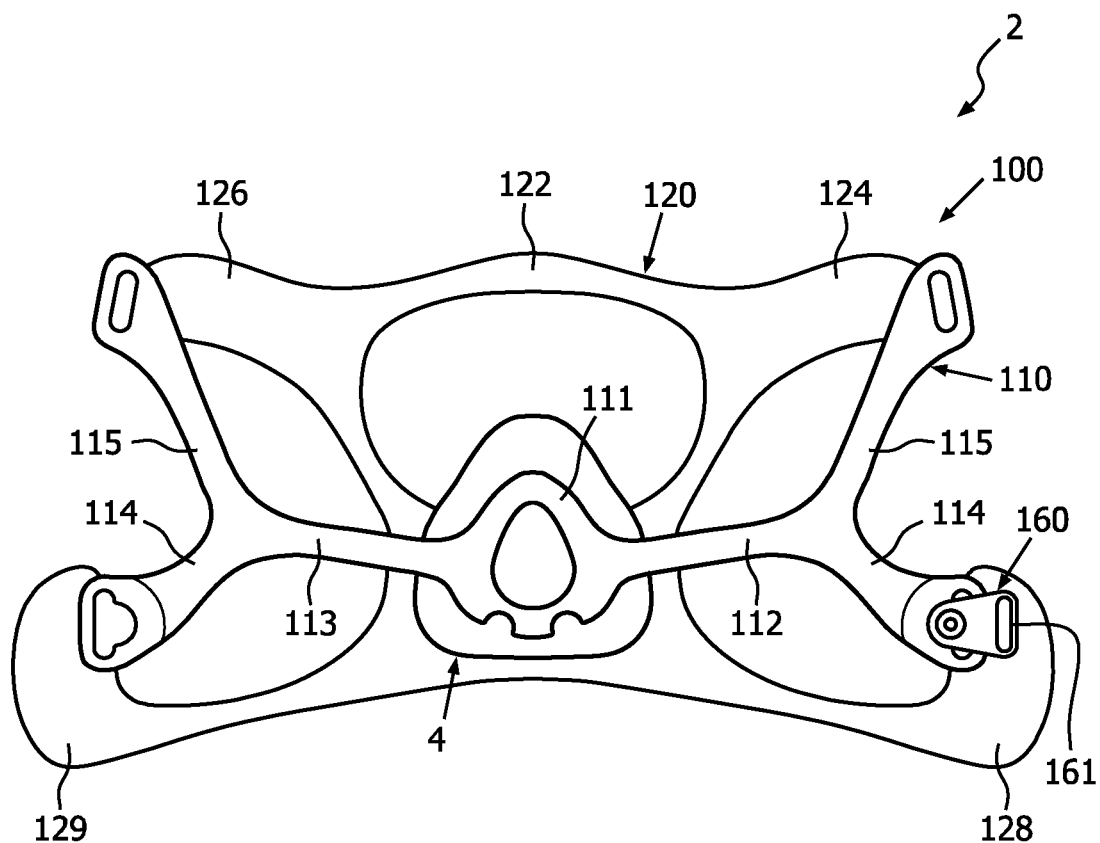
FIG. 1 is a simplified front view of a patient interface device and retention assembly therefor, in accordance with a non-limiting embodiment of the disclosed concept.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the phrase "removably coupled" means that one component is coupled with another component in an essentially temporary manner. That is, the two components are coupled in such a way that the joining or separation of the components is easy and would not damage the components. For example, two components secured to each other by a press-fit mechanism or a snap-fit mechanism are "removably coupled" whereas two components that involve welding processes, glue, or difficult to access fasteners to be joined are not "removably coupled."

As used herein, the phrase "primary disconnect location" means a location on an apparatus, such as a retention assembly, which has the greatest probability for disconnect between two removably coupled components, when the retention assembly is used in standard operating conditions. For example, when a patient interface device, which includes a retention assembly, is employed to deliver therapy to a patient in standard operating conditions, a "primary disconnect location" of the retention assembly is a location where two removably coupled components are more likely to move to a position of not being coupled than any other location on the retention assembly where removably coupled components are located.

As used herein, the phrase "secondary disconnect location" means any location where removably coupled components are located other than a primary disconnect location.

As used herein, the phrase "standard operating conditions" means typical conditions associated with delivery of pressure support therapy to a patient wearing a patient interface device including a retention assembly. For example and without limitation, "standard operating conditions" include when a patient is sleeping in bed and ordinary external forces (e.g., without limitation, due to contact with a pillow) are applied to the retention assembly. "Standard operating conditions" do not include the application of extraneous external forces (e.g., without limitation, forces due to the hands of the patient and/or an external tool) to components of the retention assembly.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 shows a patient interface device 2 that includes a cushion member 4 and a retention assembly 100 according to an exemplary embodiment. When patient interface device 2 is employed to deliver pressure support therapy to a patient, cushion member 4 engages the face of the patient and retention assembly 100 maintains cushion member 4 on the face of the patient. More specifically, retention assembly 100 includes a retention member such as the example flexible mask frame 110. Mask frame 110 includes a central portion 111 that is coupled to cushion member 4, and a pair of Y-shaped side arms 112,113 extending from central portion 111. Side arm 112 has a first branch member 114 and a second branch member 115. Side arm 113 likewise has a pair of branch members 114,115, as shown.

Figure 2:
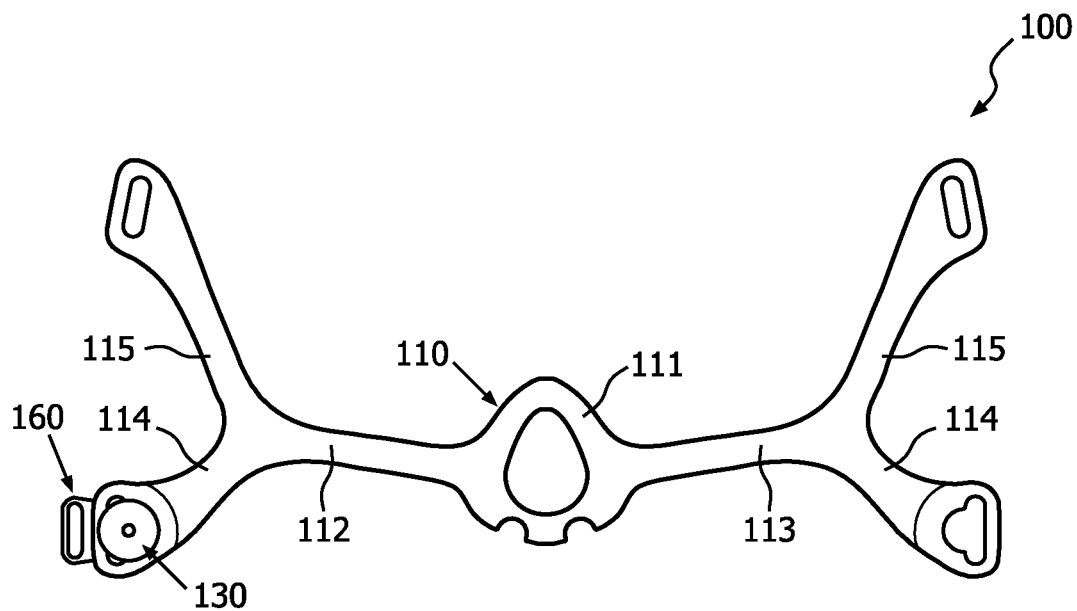
FIG. 2 is a rear view of the retention assembly of FIG. 1, and shown without a headgear member.

Retention assembly 100 further includes a headgear member such as the example headgear component 120, a first interconnect member 130 (shown in FIG. 2), and a second interconnect member 160. As described in detail herein, first interconnect member 130 and second interconnect member 160 together define a coupling assembly for retention assembly 100. Headgear component 120 includes a back portion 122 that is structured to engage the back of the head of the patient, a pair of top strap members 124,126 and a pair of bottom strap members 128,129 each extending from back portion 122. Top strap members 124,126 are each removably coupled to corresponding second branch members 115 of side arms 112,113. As described in greater detail herein, first interconnect member 130 is removably coupled to first branch member 114 of side arm 112 of mask frame 110, and second interconnect member 160 is removably coupled to first bottom strap member 128 of headgear component 120. For ease of illustration and economy of disclosure, only a single set of interconnect members 130,160 are shown in the FIGS. and described in detail herein, although it will be appreciated that retention assembly 100 further includes another pair of interconnect members (not shown) substantially the same, and configured substantially the same, as interconnect members 130,160, that are removably coupled to the corresponding first branch member 114 of side arm 113 and second bottom strap member 129. As will be discussed in greater detail below, interconnect members 130,160 are structured to be removably coupled to one another in order to couple headgear component 120 to mask frame 110.

Interconnect members 130,160 also provide a relatively quick and reliable mechanism for assembling and disassembling retention assembly 100 under standard operating conditions. For example, interconnect members 130,160 provide a simple mechanism to recouple mask frame 110 to headgear component 120 in the middle of the night in the event of an inadvertent decoupling (i.e., due to shifting of the patient's head on a pillow). Furthermore, first interconnect member 130 may advantageously be coupled and decoupled to mask frame 110 with no modification required to mask frame 110 or first interconnect member 130.

Figure 3:
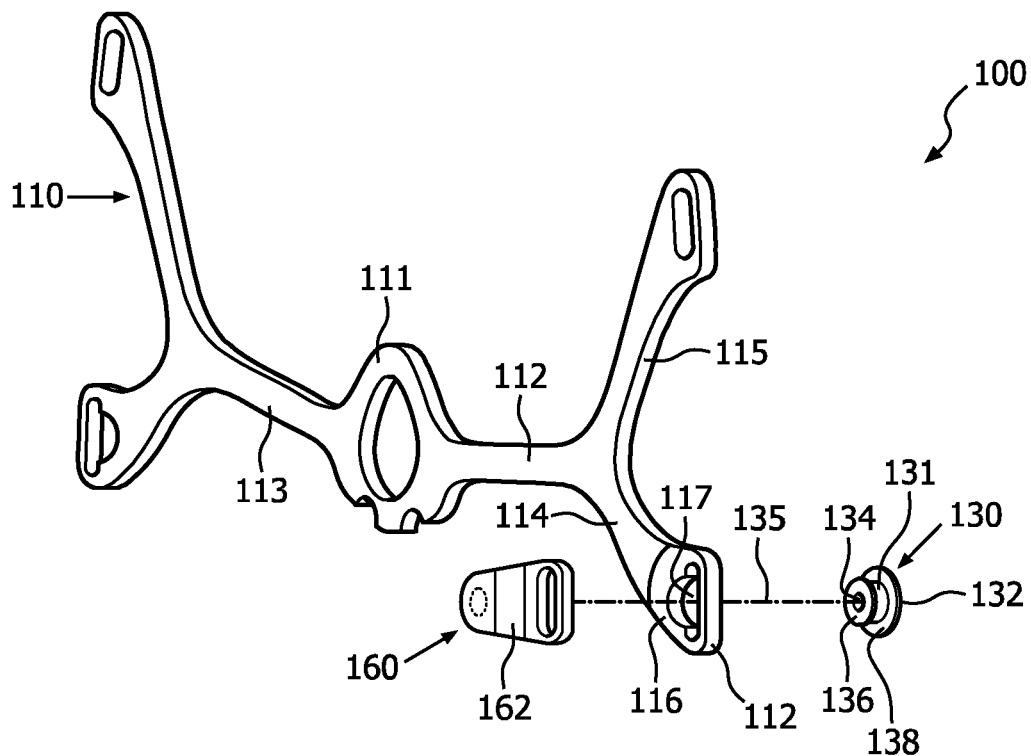
FIG. 3 and FIG. 4 are exploded views of the retention assembly of FIG. 2.
Figure 4:
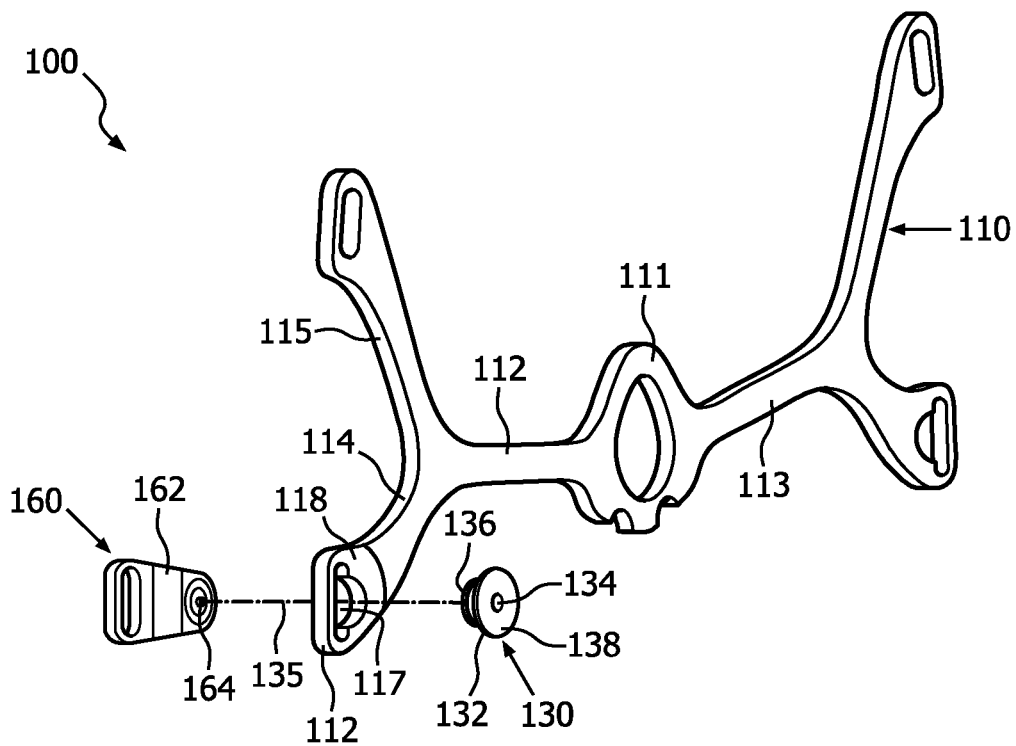
Figure 5:
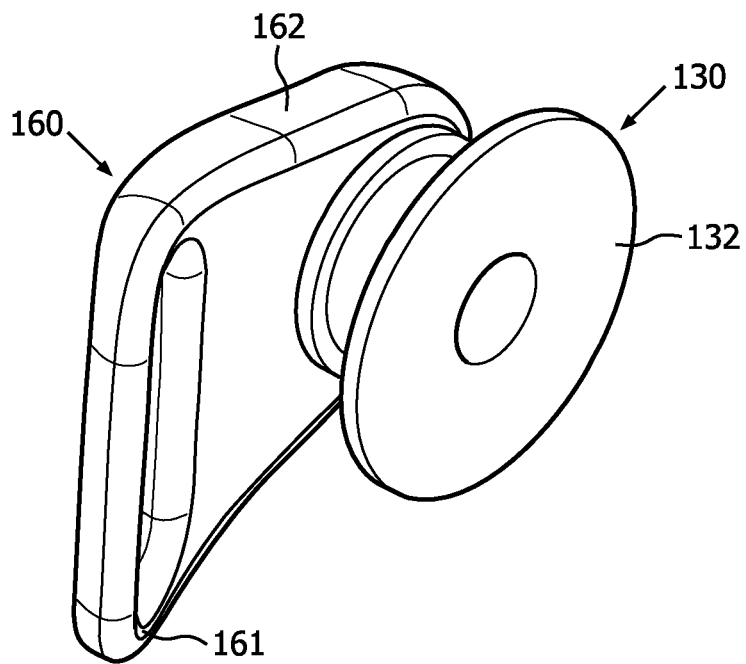
FIG. 5 is an isometric view of a pair of interconnect members for the retention assembly of FIG. 2.
Figures 6, 7:
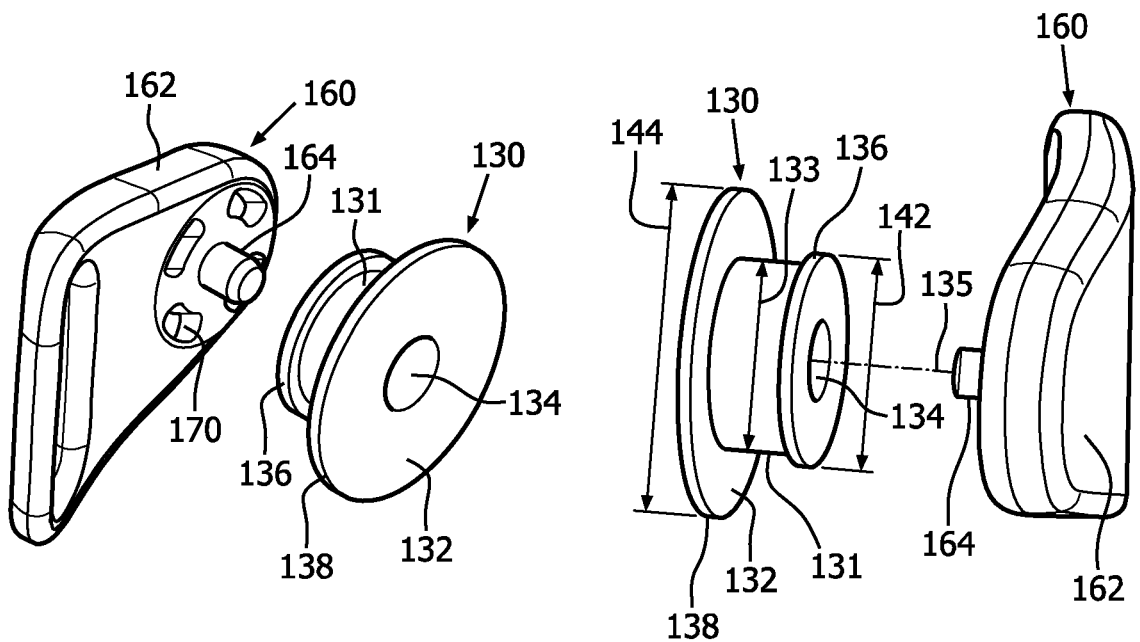
FIG. 6 and FIG. 7 are exploded isometric views of the interconnect members of FIG. 5.

FIG. 3 and FIG. 4 show exploded views of a portion of retention assembly 100, which illustrate connection of interconnect members 130,160 and which will be described in greater detail below. FIG. 5 shows an isometric view of first interconnect member 130 and second interconnect member 160 in a condition where the two components are coupled to one another, and FIGS. 6 and 7 show isometric views of first interconnect member 130 and second interconnect member 160 in a condition where the two components are not coupled to one another. Referring to FIG. 6 and FIG. 7, first interconnect member 130 includes a main body 132 having an aperture (see, for example, thru hole 134). Main body 132 includes a number of coupling portions (e.g., first blocking portion 136, second blocking portion 138, and cylindrical-shaped post 131 extending between blocking portions 136, 138). Second interconnect member 160 includes a main body 162 having a coupling portion (e.g., post 164) extending therefrom. In operation, post 164 extends into thru hole 134 proximate first blocking portion 136 in order to allow second interconnect member 160 to be removably coupled to first interconnect member 130.

Additionally, first interconnect member 130 and second interconnect member 160 each include a magnet 140,170, shown in FIG. 8. FIG. 9 shows a side view of interconnect members 130,160 and FIG. 10 shows a section view of FIG. 9. First magnet 140 is affixed to main body 132, and second magnet 170 is affixed to main body 162. More specifically, in the exemplary embodiment, main body 132 and main body 162 are each a single unitary component (e.g., a single injection molded component), wherein main body 132 is affixed to first magnet 140, and main body 162 is affixed to second magnet 170, by an overmolding process.

Referring to FIG. 10, the polarities of magnets 140,170 are oriented such that when post 164 is located in thru hole 134, and first blocking portion 136 engages second interconnect member 160, first magnet 140 and second magnet 170 are magnetically attracted to one another in order to allow second interconnect member 160 to be removably coupled to first interconnect member 130. The direct coupling between post 164 and main body 132 (i.e., extension of post 164 into thru hole 134) advantageously prevents lateral movement of second interconnect member 160 with respect to first interconnect member 130. Accordingly, magnets 140,170 provide a force to draw interconnect members 130,160 toward each other and hold interconnect members 130,160 together, and post 164 prevents interconnect members 130,160 from sliding laterally with respect to one another.

Additionally, because the primary force keeping first interconnect member 130 removably coupled to second interconnect member 160 is the magnetic attraction between magnets 140,170, a simple applied force by a hand to overcome the magnetic attraction is all that is required to decouple interconnect members 130,160 and thus disassemble retention assembly 100. Similarly, simple alignment of post 164 and thru hole 134, proximate first blocking portion 136, will result in magnets 140,170 attracting one another and pulling interconnect members 130,160 together to advantageously be removably coupled together.

Referring again to FIG. 3 and FIG. 4, first branch member 114 has a thru hole 117. Thru hole 134 has a center line 135 that extends through thru hole 117 of first branch member 114. Furthermore, when assembled, first interconnect member 130 extends through thru hole 117 and is reliably maintained on mask frame 110. More specifically, first branch member 114 includes a first side portion 116 (shown in FIG. 3) and a second side portion 118 (shown in FIG. 4) that each face away from one another in opposing directions. When assembled, blocking portions 136,138 are located on opposing sides of first branch member 114 and are structured to maintain first interconnect member 130 on mask frame 110.

That is, first blocking portion 136, which is structured for selective engagement with second interconnect member 160 as described above, is structured to engage first side portion 116 in order to prevent first interconnect member 130 from being pulled through thru hole 117. Second blocking portion 138, which is spaced from second interconnect member 160, is structured to engage second side portion 118 in order to prevent first interconnect member 130 from being pulled through thru hole 117. Moreover, because mask frame 110 is flexible (i.e., made of a fabric material and/or a flexible thermoplastic material), first interconnect member 130 is advantageously able to be removably coupled to first branch member 114 by a press-fit mechanism. In other words, during assembly, the relatively large blocking portions 136, 138 cause mask frame 110 to deform when being inserted and result in post 131 becoming seated in the generally arcuate part of hole 117.

Additionally, blocking portions 136,138 are generally disc-shaped in order to properly allow first interconnect member 130 to be removably coupled to mask frame 110. However, any suitable alternative-shaped blocking portion (e.g., without limitation, rectangular-shaped, not shown) may be employed, depending on the shape of a given mask frame (not shown). Thus, it will be appreciated that the disclosed concept is not limited to mask frame 110 and headgear component 120 for patient interface 2. Specifically, suitable alternative interconnect members (e.g., without limitation, interconnect members 330,360, shown in FIG. 11, and/or other interconnect members (not shown)) may be employed for a suitable alternative mask frame (e.g., rigid mask frames 310,510, shown in FIG. 13 and FIG. 19, respectively) and a respective headgear component 320 (FIG. 11) in order to perform the desired function of forming a reliable primary disconnect location (discussed in greater detail below).

First blocking portion 136 has a first diameter 142 (shown in FIG. 7) and second blocking portion 138 has a second diameter 144 (shown in FIG. 7) greater than first diameter 142. Additionally, post 131 has a third diameter 133 (shown in FIG. 7) less than first diameter 142 and second diameter 144. In the exemplary embodiment, second diameter 144 is at least 1 millimeter greater than third diameter 133 (in one particular embodiment, second diameter 144 is about 7.5 millimeters greater than third diameter 133), advantageously allowing a patient to be able to grip first interconnect member 130 during installation and removal from mask frame 110. As a result, the relatively large diameter 144 of second blocking portion 138 prevents first interconnect member 130 from being pulled through thru hole 117 of mask frame 110, thus ensuring that post 131 and first branch member 114 form a secondary disconnect location.

That is, post 131 is removably coupled to first branch member 114 to form a secondary disconnect location for retention assembly 100. Referring again to FIG. 1, second interconnect member 160 further includes a coupling portion 161 that is removably coupled to headgear component 120 to form another secondary disconnect location for retention assembly 100. In accordance with the disclosed concept, first blocking portion 136 is removably coupled to post 164 to form a primary disconnect location for retention assembly 100.

Thus, in standard operating conditions, when retention assembly 100 is fully assembled, the location where disconnect is most likely to occur is between first blocking portion 136 and post 164. As such, when patient interface device 2 is secured to a patient to deliver pressure support therapy and retention assembly 100 is secured to cushion member 4, post 131 and coupling portion 161 are better secured (i.e., more difficult to decouple absent extraneous external forces) to mask frame 110 and headgear component 120, respectively, than blocking portion 136 and post 164 to each other. Because the direct coupling of first interconnect member 130 to second interconnect member 160 simply requires the placement of post 164 proximate thru hole 134 (i.e., resulting in magnets 140,170 pulling interconnect members 130, 160 together), recoupling retention assembly 100 in the event of an inadvertent decoupling (i.e., due to a patient rolling on a pillow in the middle of the night) is advantageously simplified.

More specifically, known prior art clips often require properly aligning a clip (not shown) to a mask frame (not shown) in the dark, and applying a force to snap the clip (not shown) into place. Distinct from such mechanisms, retention assembly 100 simply requires positioning post 164 proximate thru hole 134 and allowing the magnetic attraction between magnets 140,170 to recouple retention assembly 100. Because first interconnect member 130 and second interconnect member 160 are removably coupled to mask frame 110 and headgear component 120, respectively, at secondary disconnect locations, positioning of post 164 proximate thru hole 134 is all that is necessary for recoupling. Accordingly, no significant application of external forces (e.g., snapping a clip onto a frame) or burdensome alignment is necessary. It can thus be appreciated that the concept disclosed herein provides an improved patient interface device 2 and retention assembly 100 therefor that quickly and reliably allows a mask frame 110 to be coupled to a headgear component 120.

Figure 11:
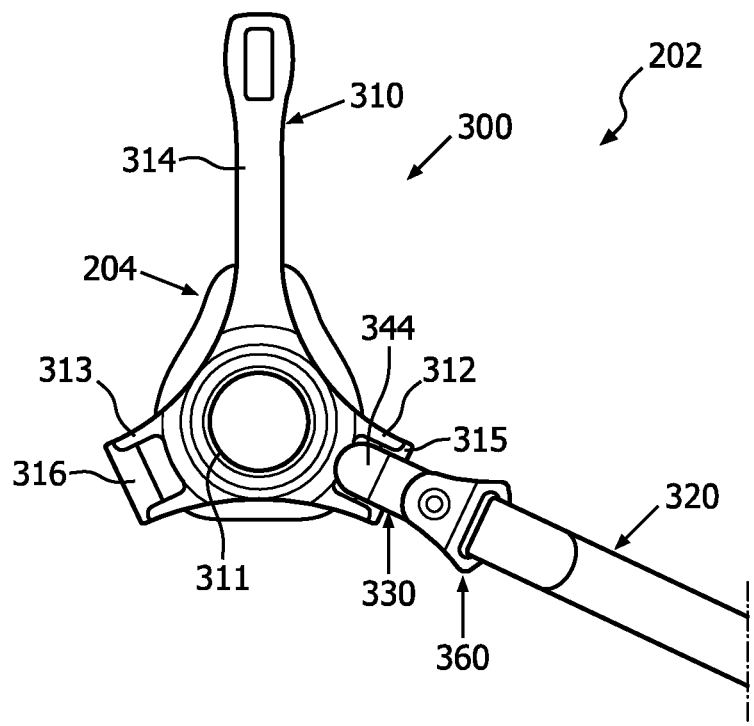
FIG. 11 and FIG. 12 are simplified front and rear views, respectively of a patient interface device and retention assembly therefor, in accordance with another non-limiting embodiment of the disclosed concept.
Figure 12:
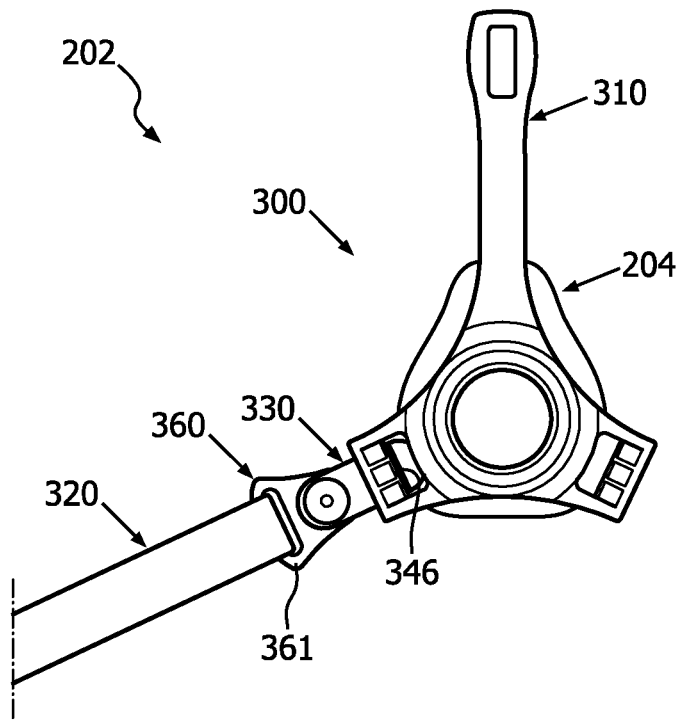

FIGS. 11 and 12 show an alternative patient interface device 202 according to an alternative exemplary embodiment. As seen FIG. 11 and FIG. 12, alternative patient interface device 202 includes many components that are similar to the patient interface device 2 (FIG. 1). For example, patient interface device 202 includes a cushion member 204 structured to engage a face of a patient when pressure support therapy is being delivered to the patient. Additionally, as will be discussed below, a first interconnect member 330 is removably coupled to a second interconnect member 360 to provide a coupling assembly in substantially the same manner as interconnect members 130,160, described above. However, different from patient interface device 2 (FIG. 1), patient interface device 202 includes a retention assembly 300 that includes a rigid mask frame 310 that is not structured to deform in order to be removably coupled to first interconnect member 330. As such, first interconnect member 330 is structured to deform in order to be removably coupled to mask frame 310.

Figure 13:
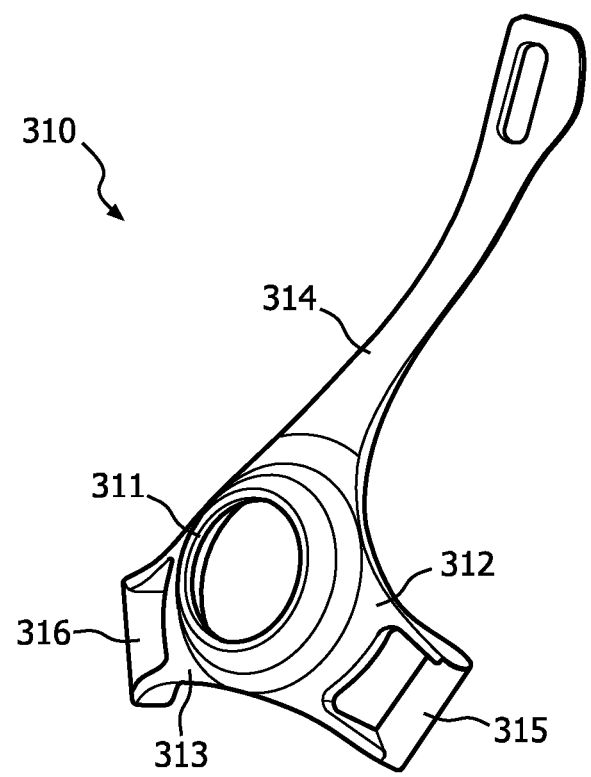
FIG. 13 is an isometric view of a retention member for the retention assembly of FIG. 11 and FIG. 12.
Figure 14:
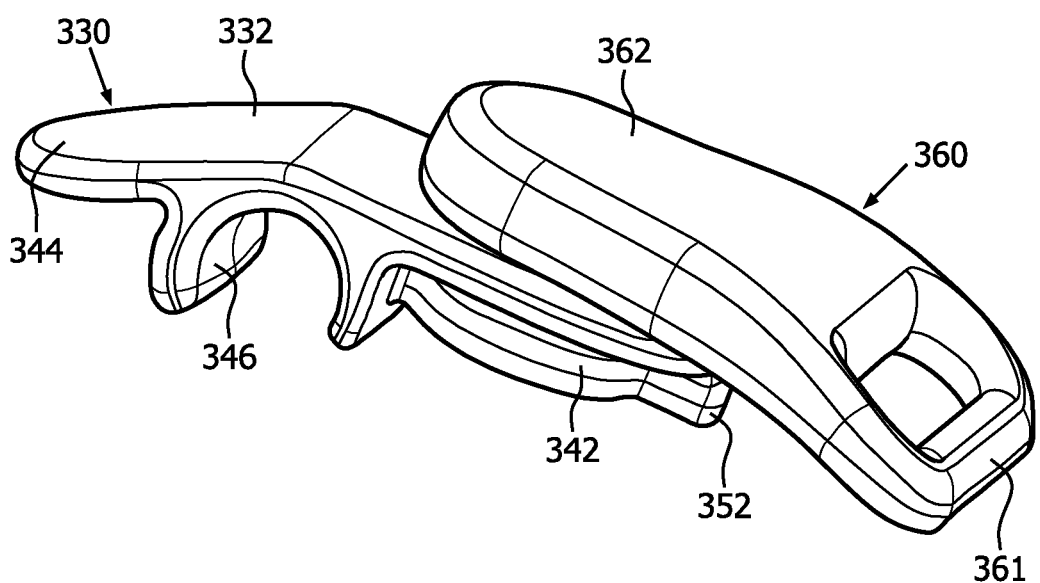
FIG. 14 and FIG. 15 are isometric views of a pair of interconnect members for the retention assembly of FIG. 11 and FIG. 12.
Figure 15:
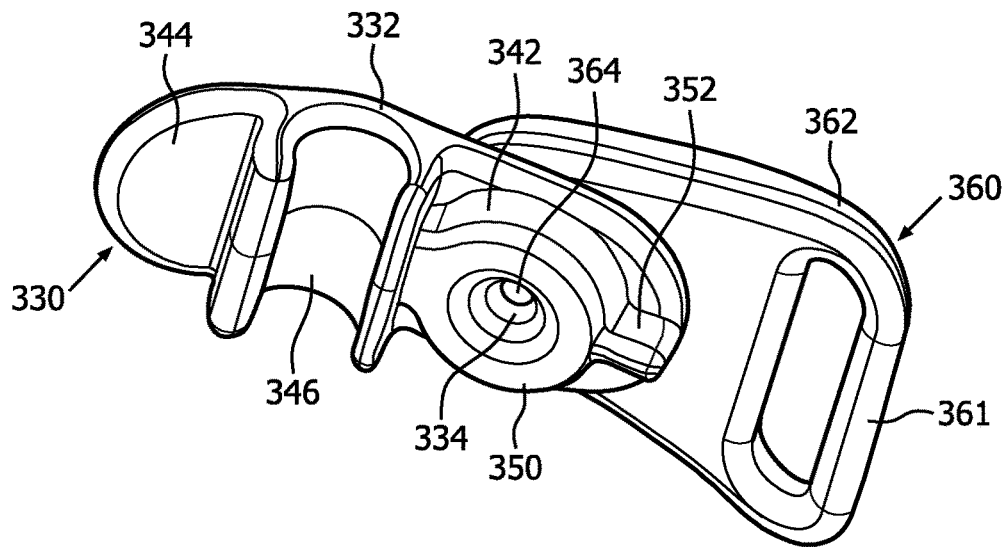

Referring to FIG. 13, mask frame 310 includes a central portion 311 and a number of arms 312,313,314 extending from central portion 311. Arms 312,313 each include a respective latch portion 315,316. FIG. 14 and FIG. 15 show isometric views of first interconnect member 330 and second interconnect member 360. Main body 332 of first interconnect member 330 includes a receiving portion 342, a blocking portion 344, and a coupling portion (e.g., hook portion 346). Hook portion 346 is located between receiving portion 342 and blocking portion 344. Furthermore, hook portion 346 is removably coupled to latch portion 315 (FIG. 13) by a snap-fit mechanism. For ease of illustration and economy of disclosure, only interconnect members 330,360 will be described in detail herein, although it will be appreciated that retention assembly 300 further includes another pair of interconnect members (not shown) substantially the same, and configured substantially the same, as interconnect members 330,360, that are removably coupled to latch portion 316 (FIG. 13) of arm 313 and headgear component 320. It will also be appreciated that arm 314 is structured to be coupled to a support member (not shown) that engages the forehead of the patient.

Figure 17:
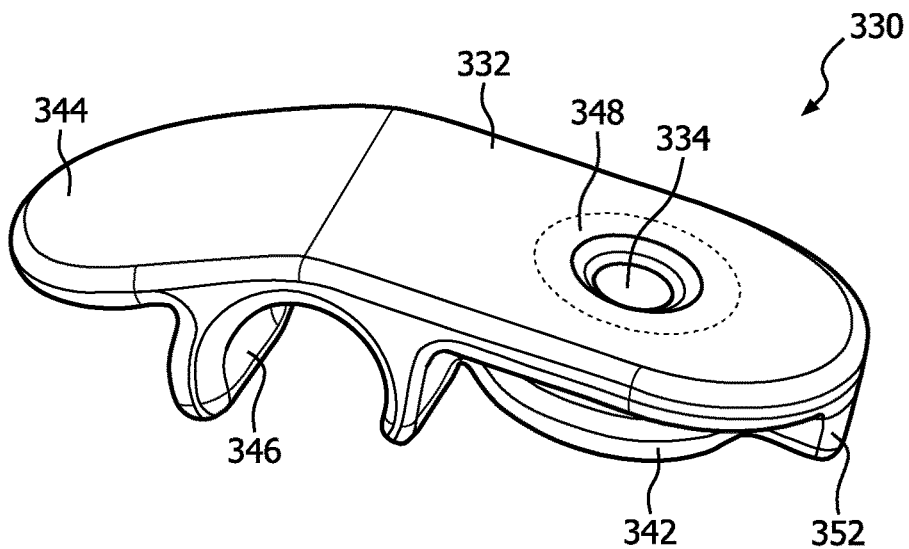
FIG. 17 and FIG. 18 are isometric and front views, respectively, of an interconnect member for the retention assembly of FIG. 11 and FIG. 12.

First interconnect member 330 may be coupled and decoupled to mask frame 310, as well as other mask frames (e.g., mask frame 510, shown in FIG. 19) that include a suitable latch portion for hook portion 346 to snap onto, without requiring modification to mask frame 310 (or mask frame 510, FIG. 19) or first interconnect member 330. Receiving portion 342 has a thru hole 334 that receives a post 364 (shown in FIG. 15) of second interconnect member 360 in substantially the same manner as thru hole 134 that receives post 164, discussed above. More specifically, receiving portion 342 has a first side portion 348 (shown in FIG. 17) and a second side portion 350 (shown in FIG. 15) that each face away from one another in opposing directions. Post 364 extends through first side portion 348.

Figure 16:
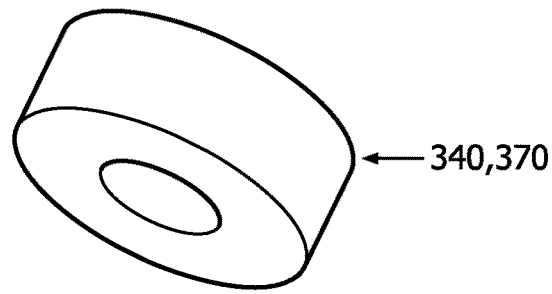
FIG. 16 is an isometric view of a magnet for the interconnect members of FIG. 14 and FIG. 15.

Additionally, first interconnect member 330 and second interconnect member 360 each include a magnet 340,370, shown in FIG. 16. Second interconnect member 360 includes a main body 362 having a coupling portion (e.g., post 364) extending therefrom. It will be appreciated that first magnet 340 and second magnet 370 are magnetically attracted to each other in order to allow second interconnect member 360 to be removably coupled to first interconnect member 330. That is, when post 364 is positioned proximate thru hole 334 at first side portion 348, magnets 340,370 draw (i.e., magnetically attract) interconnect members 330,360 toward each other, and the direct coupling between post 364 and receiving portion 342 advantageously prevents lateral movement of first interconnect member 330 with respect to second interconnect member 360.

Additionally, blocking portion 344 is structured to engage mask frame 310 in order to maintain engagement between second interconnect member 360 and first side portion 348. More specifically, and with reference to FIG. 11, blocking portion 344 engages mask frame 310 in order to prevent undesirable over-rotation of first interconnect member 330, which in the depicted orientation is out of the page. That is, the only direction in which first interconnect member 330 can rotate with respect to mask frame 310, when it is in the operating position depicted in FIG. 11, is into the page. In this manner, alignment capabilities of retention assembly 300 are advantageously improved.

Stated differently, due to the polarities of magnets 340, 370, first side portion 348 (FIG. 17) is structured to face second interconnect member 360 and receive post 364. By having blocking portion 344 engage mask frame 310 and prevent first side portion 348 from being inaccessible (i.e., due to over-rotation), post 364 is advantageously able to properly be oriented with respect to first interconnect member 330, and first magnet 340 able to be magnetically attracted to second magnet 370 to removably couple interconnect members 330,360 together.

Similar to retention assembly 100, described above, retention assembly 300 has a number of secondary disconnect locations and a reliable primary disconnect location. Specifically, hook portion 346 is removably coupled to latch portion 315 to form a secondary disconnect location for retention assembly 300. Second interconnect member 360 includes a coupling portion 361 removably coupled to headgear component 320 to form a secondary disconnect location for retention assembly 300. Additionally, first side portion 348 of first interconnect member 330 and post 364 are removably coupled to one another to form a primary disconnect location for retention assembly 300.

The primary disconnect location for retention assembly 300 is reliable in that all that is required to reassemble retention assembly 300 in the event of an inadvertent decoupling (i.e., due to a patient moving on a pillow in the middle of the night) is the positioning of post 364 proximate thru hole 334 at first side portion 348. Such slight positioning results in magnets 340,370, which also aide in positioning, pulling interconnect members 330,360 together and recoupling retention assembly 300. Thus, burdensome alignment methods (determining which position to orient a clip (not shown) with respect to a mask frame (not shown)) and applications of undesirable forces (snapping a clip back into place) in the middle of the night are advantageously minimized.

Figure 18:
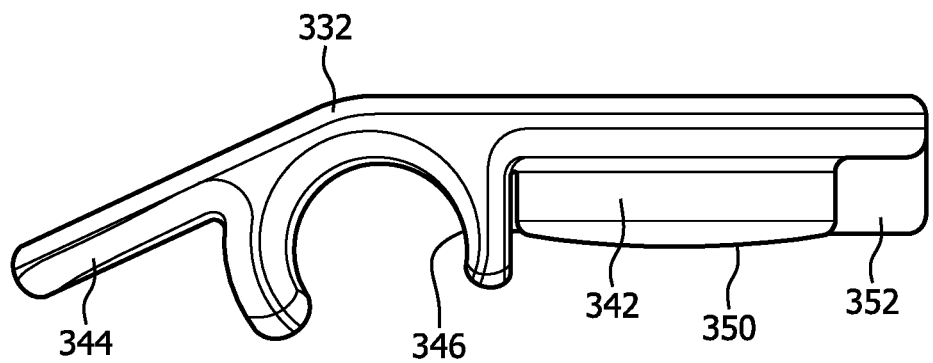
Figure 19:
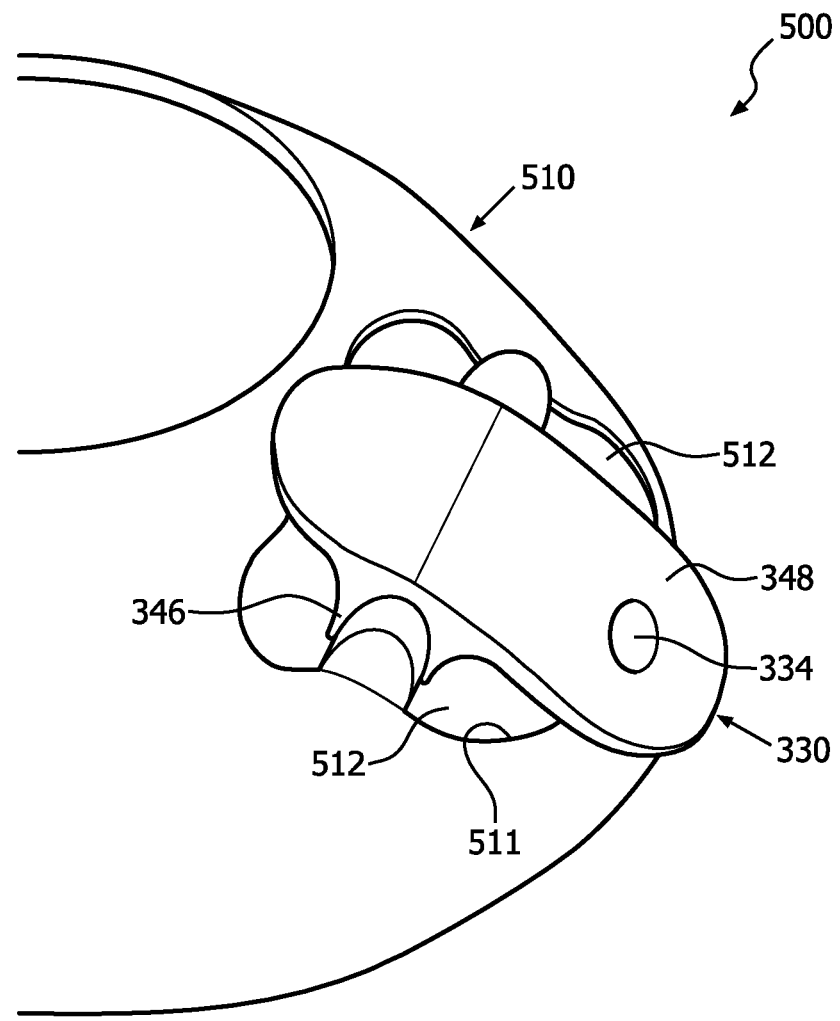
FIG. 19 is an isometric view of a portion of a retention assembly, in accordance with another non-limiting embodiment of the disclosed concept.

Referring to FIG. 18, main body 332 further includes a ridge portion 352 extending from second side portion 350. FIG. 19 shows a portion of an alternative non-limiting example retention assembly 500. Retention assembly 500 includes a retention member such as the example rigid mask frame 510, and first interconnect member 330. Mask frame 510 has an edge portion 511 defining an opening 512. It will be appreciated that ridge portion 352 of first interconnect member 330 advantageously engages edge portion 511 in order to prevent first interconnect member 330 from extending into opening 512. In this manner, first interconnect member 330 is advantageously raised up enough, with respect to mask frame 510, so that mask frame 510 is not interfered with in operation. It can thus be appreciated that the concept disclosed herein provides an improved patient interface device 202 and retention assembly 300,500 therefor that quickly and reliably allows a mask frame 310,510 to be coupled to a headgear component 320.

Additionally, although the disclosed concept has been described in detail herein with respect to magnets 140,170, 340,370 being the primary force to hold interconnect members 130,160,330,360 together, it will be appreciated that other suitable attachment mechanisms may be employed in order to perform the desired function of forming a reliable primary disconnect location and allowing interconnect members (not shown) to be removably coupled together, without departing from the scope of the disclosed concept. Furthermore, although the disclosed concept has been described in association with first interconnect members 130,330 and second interconnect members 160,360 for mask frames 110,310,510, it will be appreciate interconnect members 130,160,330,360, or suitable alternative interconnect members (not shown) may be employed with other mask frames (not shown) without departing from the scope of the disclosed concept.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A retention assembly for a patient interface device, the patient interface device comprising a cushion member structured to engage a face of a patient, the retention assembly comprising:
   a retention member structured to be coupled to and hold the cushion member, wherein the retention member has a branch member having a thru hole extending through a distal end of the branch member, and wherein the branch member has a first side portion and a second side portion each facing away from one another in opposing directions;
   a headgear member having a strap member;
   a first interconnect member structured to be removably coupled to the retention member, wherein the first interconnect member comprises a first body having an aperture, wherein the first body is structured to be received through the thru hole and held by the distal end of the branch member, wherein the first body comprises a first blocking portion and a second blocking portion, wherein the first blocking portion is structured to engage the first side portion in order to prevent the first interconnect member from being pulled through the thru hole, and wherein the second blocking portion is structured to engage the second side portion in order to prevent the first interconnect member from being pulled through the thru hole; and
   a second interconnect member structured to be removably coupled to an end of the strap member, the second interconnect member being removably coupled to the first interconnect member in order to couple the headgear member to the retention member, wherein the second interconnect member comprises a second body and a post extending therefrom, and wherein the post is structured to extend into the aperture in order to allow the second interconnect member to be removably coupled to the first interconnect member.

2. The retention assembly according to claim 1, wherein the first interconnect member further comprises a first magnet affixed to the first body; wherein the second interconnect member further comprises a second magnet affixed to the second body; and wherein the second magnet is magnetically attracted to the first magnet in order to allow the second interconnect member to be removably coupled to the first interconnect member.

3. The retention assembly according to claim 1, wherein each of the first blocking portion and the second blocking portion is disc-shaped; wherein the first blocking portion has a first diameter; wherein the second blocking portion has a second diameter greater than the first diameter; wherein the first blocking portion engages the second interconnect member; and wherein the second blocking portion is spaced from the second interconnect member.

4. The retention assembly according to claim 1, wherein the retention member is a flexible mask frame; and wherein the first interconnect member is removably coupled to the flexible mask frame by a press-fit mechanism.

5. The retention assembly according to claim 1, wherein the retention member is a rigid mask frame; and wherein the first interconnect member is removably coupled to the rigid mask frame by a snap-fit mechanism.

6. A retention assembly for a patient interface device, the patient interface device comprising a cushion member structured to engage a face of a patient, the retention assembly comprising:
  a retention member structured to be coupled to and hold the cushion member;
  a headgear member having a strap member;
  a first interconnect member structured to be removably coupled to the retention member, wherein the first interconnect member comprises a first body having an aperture; and
  a second interconnect member structured to be removably coupled to an end of the strap member, the second interconnect member being removably coupled to the first interconnect member in order to couple the headgear member to the retention member, wherein the second interconnect member comprises a second body and a post extending therefrom, and wherein the post is structured to extend into the aperture in order to allow the second interconnect member to be removably coupled to the first interconnect member;
  wherein the first body comprises a receiving portion and a blocking portion; wherein the receiving portion has a first side portion and a second side portion each facing away from one another in opposing directions, wherein the receiving portion has the aperture, wherein the first body further comprises a hook portion disposed between the receiving portion and the blocking portion along a longitudinal axis of the first body, wherein the hook portion is structured to be removably coupled to the retention member in a manner such that the first body is rotatable relative to the retention member about a rotation axis that is perpendicular to the longitudinal axis of the first body, and wherein the blocking portion is structured to engage the retention member in order to limit rotation of the first body relative to the retention member.

7. The retention assembly according to claim 6, wherein the retention member has a latch member having a rounded portion, wherein the rounded portion is structured to be received within the hook portion to permit the first body to rotate about the latch member.

8. The retention assembly according to claim 7, wherein the first body further comprises a ridge portion extending from the second side portion; wherein the retention member has an edge portion defining an opening; and wherein the ridge portion is structured to engage the edge portion in order to prevent the first interconnect member from extending into the opening.

9. The retention assembly according to claim 6, wherein the first interconnect member further comprises a first magnet affixed to the first body; wherein the second interconnect member further comprises a second magnet affixed to the second body; and wherein the second magnet is magnetically attracted to the first magnet in order to allow the second interconnect member to be removably coupled to the first interconnect member.

10. A patient interface device comprising:
  a cushion member structured to engage a face of a patient; and
  a retention assembly structured to be coupled to and hold the cushion member, the retention assembly comprising:
    a retention member structured to be coupled to and hold the cushion member, wherein the retention member has a branch member having a thru hole extending through a distal end of the branch member, and wherein the branch member has a first side portion and a second side portion each facing away from one another in opposing directions;
    a headgear member having a strap member;
    a first interconnect member structured to be removably coupled to the retention member, wherein the first interconnect member comprises a first body having an aperture, wherein the first body is structured to be received through the thru hole and held by the distal end of the branch member, wherein the first body comprises a first blocking portion and a second blocking portion, wherein the first blocking portion is structured to engage the first side portion in order to prevent the first interconnect member from being pulled through the thru hole, and wherein the second blocking portion is structured to engage the second side portion in order to prevent the first interconnect member from being pulled through the thru hole; and
    a second interconnect member structured to be removably coupled to an end of the strap member, the second interconnect member being removably coupled to the first interconnect member in order to couple the headgear member to the retention member, wherein the second interconnect member comprises a second body and a post extending therefrom, and wherein the post is structured to extend into the aperture in order to allow the second interconnect member to be removably coupled to the first interconnect member.

11. A patient interface device comprising:
  a cushion member structured to engage a face of a patient; and
  a retention assembly structured to be coupled to and hold the cushion member, the retention assembly comprising:
    a retention member structured to be coupled to and hold the cushion member;
    a headgear member having a strap member;
    a first interconnect member structured to be removably coupled to the retention member, wherein the first interconnect member comprises a first body having an aperture; and
    a second interconnect member structured to be removably coupled to an end of the strap member, the second interconnect member being removably coupled to the first interconnect member in order to couple the headgear member to the retention member, wherein the second interconnect member comprises a second body and a post extending therefrom, and wherein the post is structured to extend into the aperture in order to allow the second interconnect member to be removably coupled to the first interconnect member;

wherein the first body comprises a receiving portion and a blocking portion; wherein the receiving portion has a first side portion and a second side portion each facing away from one another in opposing directions, wherein the receiving portion has the aperture, wherein the first body further comprises a hook portion disposed between the receiving portion and the blocking portion along a longitudinal axis of the first body, wherein the hook portion is structured to be removably coupled to the retention member in a manner such that the first body is rotatable relative to the retention member about a rotation axis that is perpendicular to the longitudinal axis of the first body, and wherein the blocking portion is structured to engage the retention member in order to limit rotation of the first body relative to the retention member.

* * * * *